(12) United States Patent
Seifarth et al.

(10) Patent No.: US 11,052,127 B2
(45) Date of Patent: Jul. 6, 2021

(54) HSP FOR USE IN TREATMENT FOR IMIQUIMOD RELATED SIDE EFFECTS

(71) Applicant: Alfa Biogene International B.V., Bad Bentheim (DE)

(72) Inventors: Federico G. Seifarth, Bad Bentheim (DE); Julia Lax, Bad Bentheim (DE)

(73) Assignee: Alfa Biogene International B.V., Bad Bentheim (DE)

( * ) Notice: Subject to any disclaimer, the term of this patent is extended or adjusted under 35 U.S.C. 154(b) by 0 days.

(21) Appl. No.: 16/202,657

(22) Filed: Nov. 28, 2018

(65) Prior Publication Data
US 2019/0091289 A1 Mar. 28, 2019

Related U.S. Application Data

(62) Division of application No. 14/649,619, filed as application No. PCT/EP2013/075848 on Dec. 6, 2013, now Pat. No. 10,159,709.

(60) Provisional application No. 61/734,428, filed on Dec. 7, 2012.

(51) Int. Cl.

| | | |
|---|---|---|
| *A61K 38/00* | (2006.01) | |
| *A61P 17/00* | (2006.01) | |
| *A61K 38/16* | (2006.01) | |
| *A61K 36/00* | (2006.01) | |
| *C07K 1/00* | (2006.01) | |
| *C07K 14/00* | (2006.01) | |
| *C07K 14/37* | (2006.01) | |
| *C07K 16/00* | (2006.01) | |
| *C07K 17/00* | (2006.01) | |
| *A61K 8/49* | (2006.01) | |
| *A61K 8/64* | (2006.01) | |
| *A61Q 19/00* | (2006.01) | |
| *A61Q 19/06* | (2006.01) | |
| *A61K 31/437* | (2006.01) | |
| *A61K 38/01* | (2006.01) | |
| *C07K 14/415* | (2006.01) | |
| *A61K 31/4745* | (2006.01) | |

(52) U.S. Cl.
CPC .......... *A61K 38/168* (2013.01); *A61K 8/4946* (2013.01); *A61K 8/645* (2013.01); *A61K 31/437* (2013.01); *A61K 31/4745* (2013.01); *A61K 38/011* (2013.01); *A61Q 19/005* (2013.01); *A61Q 19/008* (2013.01); *A61Q 19/06* (2013.01); *C07K 14/415* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,932,571 B2 | 1/2015 | Seifarth et al. | |
| 2012/0087872 A1* | 4/2012 | Tamarkin ................. | A61K 8/46 |
| | | | 424/43 |
| 2014/0303089 A1 | 10/2014 | Lax et al. | |

FOREIGN PATENT DOCUMENTS

| | | |
|---|---|---|
| WO | 02/24220 A2 | 3/2002 |
| WO | 2010/102988 A1 | 9/2010 |

OTHER PUBLICATIONS

"Prophylactic," available online at https://www.dictionary.com/browse/prophylactic, 5 pages (accessed on Jan. 4, 2020) (Year: 2020).*
Stanford Health Care, "Can you prevent psoriasis?", available online at https://stanfordhealthcare.org/medical-conditions/skin-hair-and-nails/psoriasis/prevention.html, 2 pages (2019) (Year: 2019).*
Cleveland Clinic, "Psoriasis: Prevention," available online at https://my.clevelandclinic.org/health/diseases/6866-psoriasis/prevention, 4 pages (2016) (Year: 2016).*
NDA for Aldara™, available online at https://www.accessdata.fda.gov/drugsatfda_docs/label/2005/020723s018lbl.pdf, 27 pages (2005) (Year: 2005).*
Park et al., Plant Pathol. J. 31:323-333 (2015) (Year: 2015).*
NCBI Database, Gen Bank Accession No. AAV98051.1, 2 pages (2008) (Year: 2008).*
BLAST sequence comparison between HSP70 from Medicago sativa and *Arabidopsis thaliana*, 4 pages (performed on Jul. 10, 2020) (Year: 2020).*
BO Biosciences, "Hydrolysis to Hydrolysate", available online at https://www.bdbiosciences.com/documents/Hydrolysis_to_Hydrolysate.pdf, 2 pages (2009).
Borges et al., Frontiers Immunology 3:1-12 (May 2012).
Cantisani Carmen et al: "Imiquimod 5% cream use in dermatology, side effects and recent patents.",Recent Patents on Inflammation & Allergy Drug Discovery Jan. 2012,vol. 6, No. 1, Jan. 2012 (Jan. 2012), pp. 65-69, XP002720242,1SSN: 1872-213X.

(Continued)

*Primary Examiner* — Thea D' Ambrosio
(74) *Attorney, Agent, or Firm* — Banner & Witcoff, Ltd.

(57) ABSTRACT

The invention relates to a healthcare product comprising (i) a component selected from the group of heat shock proteins from alfalfa and heat shock protein hydrolysates from alfalfa, the product further comprising imiquimod

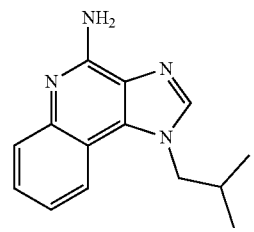

or a pharmaceutically acceptable salt or derivative thereof. Further, the invention relates to a healthcare product for use in the prophylactic or therapeutic treatment of a skin disorder. Further, the invention relates to HSP for use for use in preventing the occurrence of a negative-side effect of a treatment with imiquimod, or alleviating such side effect.

5 Claims, 1 Drawing Sheet

(56) References Cited

OTHER PUBLICATIONS

Chuang Chi-Mu et al.,"Treatment with Imiquimod enhances anti-tumor immunity induced by therapeutic HPV DNA vaccination", Journal of Biomedical Science, Kluwer Academic Publishers, DO, vol. 17, No. I, Apr. 28, 2010 (Apr. 28, 2010), p. 32, XP021071217, ISSN: 1423-0127, DOI: 10.1186/1423-0127-17-32.

Database CAPLUS, [Online] Jan. 1, 2005 (Jan. 1, 2005),Dal Farra Claude et al: "Heat shock proteins for cosmeceuticals",XP002537824,retrieved from CAPLUSDatabase accession No. 2005-269265.

International Search Report issued from corresponding PCT/EP2013/075848, dated Feb. 19, 2014.

Ma B. et al: "Current Status of Human Papillomavirus Vaccines",Journal of the Formosan Medical Association, Excerpt a Medica Asia, Hong Kong, HK,vol. 109, No. 7, Jul. 1, 2010 (Jul. 1, 2010), pp. 481-483, XP027167449,1SSN: 0929-6646 [retrieved on Jul. 1, 2010].

National Cancer Institute: "A Phase I efficacy and safety study of HPV16-specific therapeutic DNA-vaccinia vaccination in combinationwith topical imiquimod, in patients with HPV16+ high grade cervical dysplasia (CIN3)", Jun. 11, 2008 (Jun. 11, 2008), XP002719652,Retrieved from the Internet:URL:http://www.cancer.gov/clinicaltrials/search/view/print?cdrid=617261 &version= HealthProfessional[retrieved on Feb. 4, 2014].

Nishida T et al: "Geranylgeranylacetone protects against acetaminophen-induced hepatotoxicity by inducing heat shock protein 70",Toxicology, Limerick, IR,vol. 219, No. 1-3, Feb. 15, 2006 (Feb. 15, 2006), pp. 187-196, XP027919280,1SSN: 0300-483X [retrieved on Feb. 15, 2006].

Sinn D I et al: "Pharmacological induction of heat shock protein exerts neuroprotective effects in experimental intracerebral hemorrhage",Brain Research, Elsevier, Amsterdam, NL,vol. 1135, Mar. 2, 2007 (Mar. 2, 2007), pp. 167-176, XP026864911 ,ISSN: 0006-8993[retrieved on Feb. 1, 2007].

Sung et al., Physiol. Plantarium 113:443-451 (2001).

* cited by examiner

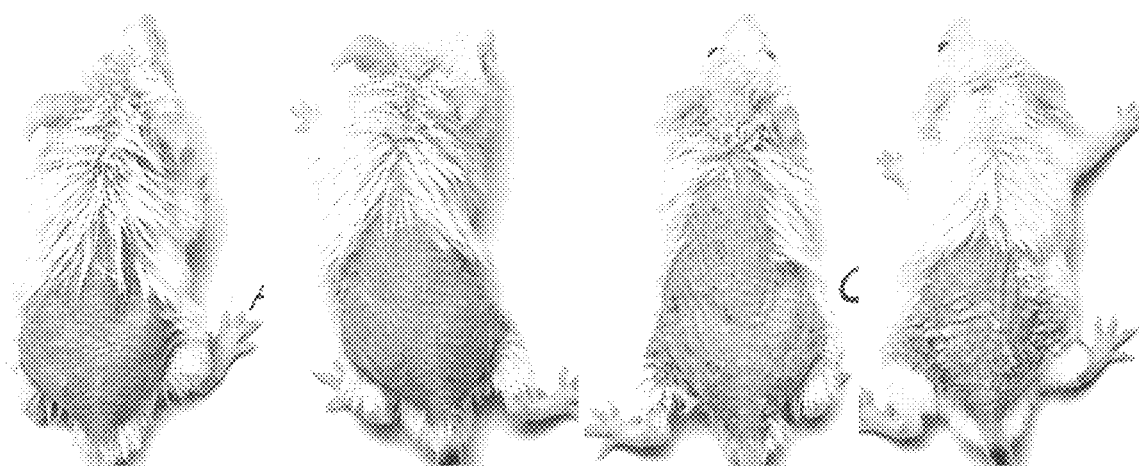

HSP FOR USE IN TREATMENT FOR IMIQUIMOD RELATED SIDE EFFECTS

RELATED APPLICATIONS

This application is a divisional application which claims priority to U.S. Patent Application No. 14/649,619, filed on Jun. 4, 2015, which is a National Stage Application under 35 U.S.C. 371 of co-pending PCT application PCT/EP2013/075848 designating the U.S. and filed Dec. 6, 2013; which claims the benefit of US provisional application number 61/734,428 filed on Dec. 7, 2012 each of which are hereby incorporated by reference in their entireties.

THE INVENTION

The invention relates to a healthcare product comprising a pharmaceutical compound for treating a skin disorder. The invention further relates to a heat shock protein (Hsp) for medical use.

Various healthcare products for treating the skin are known. The products may be purely cosmetic compositions, essentially cosmetic compositions with medical benefits, over the counter drugs or prescription drugs.

Healthcare products, such as skincare products, comprising a pharmaceutically compound can be unsatisfactory in that the effect of the treatment is less than desired (e.g. low effect or slow effect in realising the intended purpose, for instance, wound healing, treatment of infection or inflammation) or in that the pharmaceutical compound may cause an unwanted side-effect. In particular skincare products comprising a pharmaceutical compound can have a significant risk of causing skin irritation, itchiness, skin redness (erythema), scaling of the skin, or swelling of the skin.

It is an object of the invention to provide an alternative healthcare product, in particular a skincare product or an Hsp containing agent, suitable for use in the prevention or therapeutic treatment of a skin disorder. In particular it is an object to provide such product, that has satisfactory efficacy and wherein the risk of a side-effect to the skin is reduced at least for some subjects, or wherein the side-effect—if it manifests itself—is less severe or vanished within a relatively short time-span, at least for some subjects.

The inventors have found that Hsp used in combination with a specific pharmaceutical is advantageous in that the medical effect of the pharmaceutical is improved and/or in that a negative side-effect of the pharmaceutical is alleviated or the manifestation of the side-effect is avoided.

Accordingly, the present invention relates to a healthcare product comprising (i) a component selected from the group of heat shock proteins from alfalfa and heat shock protein hydrolysates from alfalfa, the product further comprising (ii) a drug suitable for treating a skin disorder.

In particular, the invention relates to a healthcare product comprising (i) a component selected from the group of heat shock proteins from alfalfa and heat shock protein hydrolysates from alfalfa, the product further comprising imiquimod or pharmaceutical acceptable salt or derivative thereof.

Imiquimod is a pharmaceutical compound represented by the following formula.

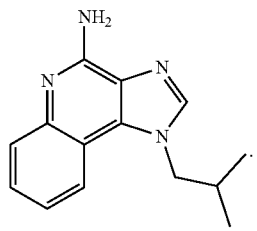 [SMILES: CC(C)Cn1cnc2c(N)nc3ccccc3c21]

The imiquimod may be provided as the free base or in a pharmaceutically active salt-form or a pharmaceutically active derivative form. As used herein a derivative means in particular a molecule formed from the reaction of the —NH$_2$ group of imiquimod with another compound, in particular a compound forming a hydrolysable group, such as an amide, with imiquimod.

The term "or" as used herein is defined as "and/or" unless specified otherwise.

The term "a" or "an" as used herein is defined as "at least one" unless specified otherwise.

When referring to a moiety (e.g. a compound) in the singular, the plural is meant to be included, unless specified otherwise.

When referring to a 'drug' or 'pharmaceutical compound', this does NOT include Hsp or Hsp hydrolysate, but to a different compound having a pharmaceutical activity in the treatment of the skin. Generally the pharmaceutical compound is a relatively small organic compound, having a molecular mass of less than 1000 g/mol. Specifically the term is used for imiquimod in all its pharmaceutically active and pharmacologically acceptable forms.

A healthcare product or Hsp containing composition according to the invention is in particular useful for the prophylactic or therapeutic treatment of a skin disorder.

In particular, the inventors have found that the use of Hsp in co-therapy with a drug applied for prophylactic or therapeutic treatment of a skin disorder is advantageous in the prophylaxis or therapeutic treatment of a negative side effect of the drug, more specifically in the prophylaxis or therapeutic treatment of a negative side effect of imiquimod. Possible side effects of imiquimod include eczema, alopecia, dermatitis, and pruritus. Remote site skin reaction has been reported and included erythema (3% in females, 1% in males), ulceration (2% in females), erosion (2% in males), edema (1% in females, 1% in males), induration (1% in males), and scaling/excoriation/flaking (1% in males). Remote site reactions reported in more than 1% of patients have included bleeding, burning, itching, pain, dryness, scabbing, crusting, redness, hardening of the skin, tenderness, and tinea cruris. Hyperkeratosis, rash, skin disorder, photosensitivity reaction, verruca, and remote site irritation have been reported. Imiquimod-induced psoriasis and at least 1 case each of vitiligo-like hyperpigmentation, contact pemphigus, pityriasis rubra pilaris exacerbation, erosive pustular dermatosis of the scalp, and eruptive keratoacanthoma have been reported. Exfoliative dermatitis, erythema multiforme, hyperpigmentation, and hypertrophic scar have been reported during postmarketing experience. Further side-effects include change of color of treated skin, headache, dizziness, chest pain, back pain, cold sores, fever blisters, cold symptoms such as stuffy nose, sneezing, sore throat, nausea, diarrhea, loss of appetite, vaginal itching or discharge, Arthritis.

In particular, it has been found that the application of Hsp is useful for avoiding or reducing the occurrence of erythema, scaling of the skin, or thickening of the skin.

Accordingly, the invention further relates to a heat shock protein, for use in preventing the occurrence of a negative side effect of a treatment with imiquimod or another drug for treating a skin disorder, or therapeutically treating such side effect. The invention has been found particularly effective for the prophylaxis of a negative side effect of imiquimod, such as scaling, or at least to reduce the severity at which a side-effect of imiquimod or another drug manifests itself.

That the product is effective in a prophylactic treatment can be verified routinely by comparing the incidence of the negative effect in a first population (e.g. a test panel of humans, or in test-animals) treated with the drug but not the Hsp and a second population (comparable with the first) treated with both the drug and the Hsp.

A product of the invention may in particular be for use in the treatment of mammal, preferably a human. The human may be an infant (<1 yr), an older child (1-12 yr), an adolescent (12-18 yr), or an adult in his early (19-39 yr), middle (40-65 yr) or late adulthood (>65 yr).

A product according to the invention may in particular be suitable for people or animals who have an impaired production of endogenous Hsp, or who are not capable of producing endogenous Hsps at all. It may for example be suitable for elderly people (more than 50, more than 60 or more than 70 years of age) or for people having scar tissue in or on their skin.

The production of an endogenous Hsp in skin of a subject is in particular considered impaired, if the start of the endogenous Hsp production after exposure of skin cells of the subject to a trigger for inducing endogenous Hsp is delayed (i.e. an increased response time) and/or if the endogenous Hsp production (per hour) is reduced, after exposure to the trigger. A particularly suitable trigger is exposure of the skin cells to a temperature of 43° C. (as described in U.S. Pat. No. 6,737,086).

The skin cells (keratinocytes and/or fibroblasts) can be taken from the subject and incubated in a manner known in the art per se. Hsp levels can be determined as described in S. Sanchez et al., Radiation Research 167 (2007) 572-580.

By comparing produced amount of endogenous Hsp and/or response time with a normal reference value (from cells with normal Hsp production, preferably from a subject of about the same age, the same sex and the same or a similar skin type), it can be established whether endogenous Hsp production is impaired. The produced amount can suitably be determined after 1 hour, after 2 hours, after three hours or after a longer exposure, depending on the minimum response time that is considered normal for a specific subject. For example, in U.S. Pat. No. 6,737,086 it was reported that in human skin cells originating from a five-year-old subject Hsp90 production occurred after 1 hour of exposure to a temperature of 43° C.

In impaired skin cells, the response time may in particular be increased by a factor of at least 1.5, at least 3, or at least 6. In impaired skin cells, the total amount of produced endogenous Hsp (after 1 hr, after 2 hrs or after 3 hrs) may in particular be reduced by a factor of at least 1.5, at least 3, or at least 6.

A product according to the invention may in particular be used to treat a skin disorder selected from the group of acne (for example adolescents), warts, athlete's foot, Lyme disease, psoriasis, lichen, ichthyosis, keratosis, Darier's disease, pustulosis, herpes (in particular herpes zoster), cellulitis, eczema (such as atopic dermatitis), neurodermatitis (such as lichen simplex chronicus, prurigo nodularis, lichen striatus or atopic dermatitis), inflammatory skin disorders and children's diseases affecting the skin (such as varicella, rubella, measles).

In an embodiment, the product is for use in the prophylactic or therapeutic treatment of a disorder selected from the group of molluscum contagiosum, vulvar intraepithelial neoplasia, and vaginal intraepithelial neoplasia.

In an embodiment, the product is for use in the prophylactic or therapeutic treatment of a disorder selected from the group of Superficial and Nodular BCC, Sclerodermiform BCC, Bowens disease, invasive squamous cell carcinoma, Lentigo Maligna, Metastatic Melanoma, Mycosis Fungoides, Keratoacanthoma, Extramammary Pagets Disease.

In an embodiment, the healthcare product or Hsp (hydrolysate) is for use in the prophylactic or therapeutic treatment of psoriasis. In a specific embodiment, the psoriasis is imiquimod-induced psoriasis.

The healthcare product according to the invention may contain a single composition for administration to an intended user comprising both Hsp (or hydrolysate thereof) and drug (imiquimod) or it may comprise two or more separately packaged compositions for administration to the intended user. Thus, the Hsp (hydrolysate) and the drug for skin treatment may but do not need to be present in the same composition.

The healthcare product usually is a skincare product, i.e. it comprises at least one component that is intended to be applied to the skin. Typically, at least the pharmaceutical compound for skin treatment, such as imiquimod, is present in a skincare composition for application to the skin. The Hsp (hydrolysate) may be present in the same skincare composition or a different skincare composition. However, it also may be administered in a different manner, notably orally or nasally.

Good results have been achieved with a product wherein Hsp and the drug for skin treatment (imiquimod) have been applied separately.

Accordingly, in an advantageous embodiment, the healthcare product contains a first container containing a first healthcare composition comprising the heat shock protein or heat shock protein hydrolysate and a second container containing a second healthcare composition comprising imiquimod.

A healthcare product, first composition or second composition that is for application to the skin may in particular be selected from the group of creams, lotions, powders, gels, foams, oils, sprays (e.g. aerosol sprays), mousses, salves, and balms.

In an advantageous embodiment, the first composition is for administration to the skin.

In particular, in case a fast response is desired, it is considered to provide a first composition for administration via the respiratory tract, preferably a composition selected from nasal sprays, composition for oral administration into the respiratory tract, such as an inhaler.

Alternative administration forms for the Hsp (hydrolysate) include compositions for oral or rectal intake into the gastro-intestinal tract or compositions for mucosal application.

In yet another embodiment, the Hsp is in a form for parenteral administration. Thus Hsp may be in a form for intravenous, intramuscular, intracutaneous or subcutaneous injection.

Generally, the Hsp or hydrolysate thereof that has been separated, in particular isolated from the source (the plant or part thereof) wherein it has been produced.

The Hsp is usually obtained from a plant, e.g. from a fluid from a plant or from a plant extract. Suitable methods to obtain the Hsp are known in the art per se, for instance from EP 1 531 160 A1.

The plant Hsp may be provided in a manner known per se. For instance, the plant Hsp may be a plant Hsp obtained by a method described in EP-A 1531160, of which the contents—in particular the claims and examples—are incorporated herein by reference.

In particular the Hsp may be a plant Hsp obtained by a method according to WO 2010/115990, of which the contents—in particular the examples, suitable process conditions and suitable materials for use in the method—are incorporated herein by reference.

Preferably, the Hsp is a natural, i.e. non-recombinant, Hsp; the Hsp-hydrolysate preferably is a hydrolysate from natural (non-recombinant) Hsp. It is contemplated that a natural Hsp or hydrolysate of natural Hsp may be tolerated better by the subject treated with the skin-care product, in particular that the risk of allergenic reactions may be less. Further, consumer acceptance may be better for non-recombinant plant Hsp.

A product according to the invention may comprise native Hsp or denaturated Hsp.

A product according to the invention may in particular comprise heat shock proteins or heat shock protein hydrolysates from alfalfa (*Medicago saliva*).

Optionally, in addition or alternatively the skin care product comprises Hsp or Hsp-hydrolysate from another plant. Other plants as a source of Hsp may in particular be selected from the group of cereals (for instance barley), soy, grasses (for instance oat), peas, beet, potato, clover and water plants (for instance an alga).

In particular, leaves of the plant may be used as source for one or more Hsps. Particularly suitable are beet tops, alfalfa leaves, barley leaves, oat leaves and potato tops.

With Hsp-hydrolysate is meant Hsp wherein part of the chemical bonds have been hydrolysed, in particular peptide bonds. Generally, for achieving an intended cosmetic or medical effect, non-hydrolysed Hsp may be particularly suitable. It is however contemplated that in some embodiments, the presence of Hsp-hydrolysate may be advantageous. For example, it is contemplated that hydrolysed Hsp may penetrate better into (the cells of) the skin.

The Hsp-hydrolysate may be prepared by, e.g., chemical hydrolysis, enzymatic hydrolysis or a combination thereof. Chemical hydrolysis may for example be performed in an aqueous medium of neutral pH, or in an aqueous medium in the presence of an acid (e.g. a strong acid such as HCl) or a base (e.g. a strong base such as NaOH). The hydrolysis (chemical and/or enzymatic) may be carried out at an elevated temperature. The enzymatic hydrolysis may in particular be performed with a proteolytic enzyme, based on technology known per se. Enzymatic hydrolysis is an effective alternative to chemical hydrolysis, because it is relatively mild in comparison to acid or alkali hydrolysis. Additionally, the inherent specificity of a specific proteolytic enzyme of choice can control the nature and extent of hydrolysis, and thus the functional properties of the end product.

The degree of hydrolysis may be chosen within wide limits. At least 10 wt. %, at least 25 wt. %, at least 50 wt. %, at least 80 wt. % or at least 90 wt. % (based on the sum of Hsp-fragments and unhydrolysed Hsp) of the Hsp-hydrolysate may be formed by Hsp fragments. Of the Hsp-hydrolysate, 100 wt. % or less, 95 wt. % or less, at least 75 wt. % or less, 50 wt. % or less or 25 wt. % or less (based on the sum of Hsp-fragments and unhydrolysed Hsp) may be formed by Hsp fragments.

The size of the fragments may be chosen within wide limits. Usually, in case a hydrolysate is present, at least 50 wt. %, in particular at least 75 wt. %, more in particular at least 90 wt. % (based on the sum of Hsp-fragments and unhydrolysed Hsp) of the hydrolysate is formed by peptides (including unhydrolysed Hsp) having at least five amino acid residues. In a specific embodiment, at least 25 wt. %, in particular at least 50 wt. %, more in particular at least 75 wt. % (based on the sum of Hsp-fragments and unhydrolysed Hsp) of the hydrolysate is formed by peptides (including unhydrolysed Hsp) having at least ten amino acid residues.

The skin-care product may in particular comprise at least one Hsp or hydrolysate thereof selected from the group of Hsp40, Hsp60, Hsp70 and Hsp90, respectively hydrolysates of any of these Hsps. In particular, Hsp70 or a hydrolysate thereof is preferred.

In a specific embodiment, Hsp40 or hydrolysate thereof is present. Hsp40 is expected to act as a co-chaperone and may thus improve the efficiency of Hsp70, for example by increasing the ATPase activity of Hsp70.

The concentration of Hsp, Hsp hydrolysate, or a mixture thereof in a product according to the invention may be chosen within wide limits, usually in the range of 0.1 µg to 1 mg per mL of the composition in which it is provided (i.e. the skin care product if it is formed of a single composition or in case of a product comprising more than one physically separated compositions, said first composition). In particular, the Hsp concentration is at least 5 µg/mL, preferably at least 20 µg/mL. In particular good results have been achieved with a concentration of about 50 µg/mL or more, more in particular about 0.2 mg/ml or more. Preferably the Hsp concentration is about 0.6 mg/mL or less, in particular about 0.5 mg/mL or less.

The concentration of imiquimod (or another drug for treatment of a skin disorder, usually is at least 0.001 mg/ml of the composition in which it is provided (i.e. the skin care product if it is formed of a single composition or in case of a product comprising more than one physically separated compositions, said second composition). Preferably, the concentration is at least 0.01 mg/ml, in particular 0.02 mg/ml or more. Usually, the concentration is 10 mg/ml or less, preferably 1 mg/ml or less in particular 0.5 mg/ml or less, more in particular 0.1 mg/ml or less.

The healthcare product, the first composition or the second composition, may further comprise known ingredients for a specific type of healthcare product, or composition, e.g. for a lip balm, for a moisturizing cream, for a body lotion, for a massage oil, for a scrub crème, for a peeling crème, for a depilatory cream. Suitable examples of known ingredients are for example UV blocking agents, preservatives, stabilizers, moisturizers, antioxidants, vitamins, fragrances, thickening agents, chalk, ceramides, emulsifiers, surfactants, minerals, alkaloids, enzymes, co-enzymes, acids, polyphenols, ceramides, herbs, plant extracts, solvents, amino acids, oil lipids, pH adjuster, salts, polysaccharides, fatty acids, flavonoids, hormones, yeast extracts, matrix metalloproteinases, peptides, emoillents.

A skin care product, the first composition or the second composition may be based on commercially available or otherwise known formulations to which the drug (imiquimod) or Hsp or Hsp-hydrolysate is added, e.g. on a known salve, (lip) balm, lotion, mousse, cream, oil, powder, gel, foam, spray. Examples of known skin care compositions are for example given in WO 01/85129 A2.

In an embodiment, the ingredients of the skin care product/composition, including the Hsp or Hsp hydrolysate (if present) or the drug (if present), are dissolved or emulsified in a lipophilic medium, which may comprise one or more components selected from the group of triglycerides, such as capric triglyceride, C18-C36 alkyl acid triglycerides; acrylates, such as C10-C30 alkyl acrylates; oils, such as olive oil, sunflower oil, sclerocarya birrea oil, lime oil, nut oil, manuka oil, mineral oil, rapeseed oil, teatree oil; hydroxyethyl urea; isodecyl laurate; fatty acids such as stearic acid; and phospholipids such as lecithine.

In particular, in a spray for application to the skin, the ingredients may be suspended or emulsified in a propellant, which may comprise one or more components selected from the group of chlorofluorocarbons such as 1,1,1,2-tetrafluoroethane, trichlorotrifluoroethane; hydrocarbon gases such as propane, isobutane and isopentane; dimethyl ether; carbon dioxide; and nitrogen gas.

In addition to the Hsp or Hsp-hydrolysate, a product according to the invention may comprise one or more other active agents, e.g. a co-chaperone for the Hsp or Hsp-hydrolysate. However, the product may also be free of such additional agents. It is contemplated that the Hsp or Hsp-hydrolysate may be capable of interacting with an endogenous (formed in situ by the subject) co-chaperone or the like.

In addition, one or more preserving agents may be present such as sorbate, benzoate, sulfite, or the like.

As will be understood by the skilled person, the composition is formulated to be safe for its intended administration.

The drug (imiquimod), Hsp or Hsp hydrolysate in a product according to the invention may be incorporated in a carrier, preferably a cosmetically or pharmaceutically acceptable carrier. It may for example be incorporated in a liposome or a microcapsule.

In the context of the invention liposomes are defined as composite structures comprising lipids, in particular phospholipids, and may contain small amounts of other molecules. The sizes of liposomes are usually in the range of 20 nm to 1000 nm. They may for example be at least 40 nm, at least 100 nm or at least 250 nm. The liposomes may for example be 800 nm or less, 600 nm or less or 400 nm or less.

It is envisaged that a carrier, in particular a liposome that comprises the drug (imiquimod), Hsp or a hydrolysate thereof may be capable of effective delivery of the drug (imiquimod) an Hsp respectively a hydrolysate thereof into cells of the skin.

It is further envisaged that incorporation of the drug (imiquimod) Hsp and/or a hydrolysate thereof in a carrier may result in an increased stability of the drug (imiquimod), Hsp respectively the hydrolysate thereof, for example because of a decreased exposure to (atmospheric) oxygen.

It is contemplated that at least in some embodiments Hsp or Hsp hydrolysate may be negatively affected by an alcohol, for instance ethanol. Accordingly, it is advantageous to use no alcohol or only as a minor component (e.g. in aqueous liquid) during the recovery process of the Hsp from the source and during the preparation of the skin-care product.

Imiquimod or another drug for treating a skin disorder,
The concentration of the drug, in particular imiquimod, is usually in the range of 0.1-10 wt. %, preferably in the range of 0.5-8 wt. %. In particular for imiquimod, the concentration is preferably in the range of 1-6 wt. %. Typical examples of formulations are a 5 wt. % lotion or cream, a 3.75 wt. % lotion or cream and a 2.5 wt. % lotion or cream.

The invention further relates to a method for the prophylactic treatment of a skin disorder. The invention further relates to the prophylaxis of a negative side-effect of a healthcare product comprising a therapeutic compound for the treatment of a skin disorder. The invention further relates to a method for the therapeutic treatment of a skin disorder. The invention further relates to the therapeutic treatment of a negative side-effect of a healthcare product comprising a therapeutic compound for the treatment of a skin disorder.

The skin disorder or side-effect in a method according to the invention is preferably selected from those mentioned herein above. Preferred products for use in the method are those as described elsewhere herein.

A method of treatment according to the invention typically comprises administering an effective dose of Hsp or Hsp hydrolysate to a subject, preferably a human. The human is generally treated with a drug for treating a skin disorder, preferably imiquimod, has been treated with a drug for treating a skin disorder, preferably imiquimod, or it is intended that the subject is to be treated with a drug for treating a skin disorder, preferably imiquimod.

Imiquimod or the other drug is typically applied to the skin. It is typically applied before, after or together with the Hsp or Hsp hydrolysate.

In a practical embodiment, said administration of Hsp or Hsp hydrolysate is a topical administration of a composition comprising Hsp or Hsp hydrolysate to a part of the skin that is/has been or is intended to be treated with imiquimod or another drug.

The treatment by administration on the skin can suitable done by e.g. spraying onto the skin, applying onto the skin by an applicator, such as a roller, a brush or a sponge, or by manual application.

In a further embodiment, the Hsp or Hsp hydrolysate is administered via the respiratory tract, nasally or orally. An advantage thereof is fast way of action. Nasally given Hsp has been shown to be present in muscles and is able to pass the blood brain barrier.

In a further embodiment the Hsp is administered into the gastro-intestinal tract, typically orally or rectally.

In a further embodiment, the Hsp is administered parentally (intravenous, intramuscular, intracutaneous or subcutaneous injection). An advantage thereof is a fast way of action.

The dosage of Hsp or hydrolysate thereof may be chosen within wide limits, depending on the intended use, the subject and the way of administration. As a rule of thumb a suitable average daily dosage is chosen in the range of 0.1 µg and 1 mg per square centimetre of treated skin. Usually, the average daily dosage is 0.5 µg per square centimetre of treated skin or more, in particular 1 µg per square centimetre of treated skin or more. Usually, the average daily dosage is 500 µg per square centimeter of treated skin or less, in particular 250 µg per square centimetre of treated skin or less.

In a further embodiment, in particular in an embodiment where the Hsp is not administered topically to the skin, the dosage may be in the range of 0.1 µg-25 mg/kg body weight, in particular in the range of 0.5 µg-15 mg/kg body weight, more in particular in the range of 2 µg-10 mg/kg body weight.

The dosage of imiquimod or other drug for treating a skin disorder thereof may be chosen within wide limits, depending on the intended use, the subject and the way of administration. As a rule of thumb a suitable average daily dosage is chosen in the range of 0.1µg and 5 mg per square centimetre of treated skin. Usually, the average daily dosage is 1 µg per square centimetre of treated skin or more, in particular 50 µg per square centimetre of treated skin or more. Usually, the average daily dosage is 4 mg per square centimetre of treated skin or less, in particular 2 mg per square centimetre of treated skin or less.

The skin care product may be administered e.g. once a week; preferably the skin care product is administered at least once a day. The product may be administered a plurality of times per day, e.g. 2-10 times, 2-6 times or 2-3 times. In case the product comprises more than one compositions (such as the first composition comprising the Hsp (hydrolysate) or the second composition comprising the drug, such as imiquimod), the compositions do not need to be administered the same number of times per week or day.

Good results have been achieved with a method wherein first a first composition comprising Hsp or Hsp hydrolysate is administered, and wherein thereafter a second composition comprising the imiquimod or other drug is administered.

Good results have been achieved with a method wherein there is a time-interval between administration in order to allow the Hsp to be included in the skin. The interval may in particular be chosen between 1 min and 8 hours, more in particular between 30 min and 6 hours, more in particular between 1 hour and 4 hours.

In a practical embodiment, Hsp is applied at the same time as imiquimod or the other drug.

In an advantageous embodiment, another dosage of a composition comprising Hsp or Hsp hydrolysate is given after administration of the composition comprising imiquimod or other drug. The interval between the subsequent dosage of Hsp (hydrolysate) and imiquimod or other drug can be chosen in the same range as for the interval between the Hsp (hydrolysate) dosage preceding the administration of the drug and said administration.

A dosage regime as described above advantageously repeated at least once a day.

The product or a component thereof (such as the first composition comprising the Hsp (hydrolysate) or the second composition comprising the drug, such as imiquimod) may be present in or on a plaster that is applied on at least a part of the skin that is in need of treatment. Advantageously, such plaster gradually releases the amount of skin care product that is intended to administered, for example in 24 hours or less, in 12 hours or less, in 6 hours or less or in 3 hours or less.

The invention will be illustrated by the following example.

EXAMPLE: TOPICAL ALFALFA-DERIVED HSP70 FOR TREATMENT OF A SKIN DISORDER

Materials

Imiquimod was provided in a commercially available cream (Fougera, a cream comprising 5% Imiquimod).

HSP70 (from alfalfa) was obtained from Alfa Biogene International B.V. It was dispersed in a concentration of 50 or 250 µg/ml in a carrier cream from Deutscher Apotheken Index. Said carrier cream contained (per 100 g):
  4.0 g Glycerolmonostearate 60
  6.0 g Cetylalcohol
  7.5. g Medium-chain Triglycerides
  25.5 g White Petrolatum
  7.0 g Macrogol-20-glycerolmonostearate
  10.0 g Propylene-glycol
  40.0 g Purified water Methods The effect of HSP was tested on mice (BALBc mice, male 10-12 weeks old)

The mice were divided in 5 groups of eight mice each:

Group 1: mice were treated for 6 days on shaved back and right ear with one daily application of imiquimod 5% cream to the skin (3.125 mg daily dose)

Group 2: mice were treated for 6 days as group 1. In addition the part of the skin to which imiquimod was applied was treated twice daily with the cream comprising 50 µg/ml HSP (20 µg HSP per dose). Each day, the cream comprising HSP70 was applied to the skin in a 1 mm layer, 4 hours before application of the imiquimod, and again 4 hours after treatment with imiquimod.

Group 3: mice were treated for 6 days as group 2, except for the cream comprising 250 µg/ml HSP (100 µg HSP per dose)

Group 4: mice were treated as group 2 except for the carrier cream comprising no Hsp70. (mice were treated for six days, twice a day, once four hours before treatment with imiquimod, once four hours after treatment with imiquimod.

Group 5: control group, no cream application.

Study Protocol:

Day 1: initial evaluation for visible signs of psoriasis. All visible signs were categorized and scored by a PASI score (PASI: psoriasis area and severity index) from 0-4 (erythema, scales, thickness, cumulative score: maximum of 12 points). Animal backs were shaved and photographs were taken.

Thickness of both ear pinnae were measured. Cream application was performed
according to the categorization into above detailed groups.

Day 2-6: Animals in the treatment groups were treated with the according skin
creams. All animals were assessed and examined once daily for behavioural changes and adverse effects. Ear pinnae measurements are performed daily. Skin changes
were assessed by the PASI score. On day 7, photographs of all animals (backs) were taken to document progression of the disease.

Day 7: The animals were euthanized and skin tissue and blood was processed. Inflammatory markers were measured with Q-PCR (skin samples). Skin samples were histologically examined.

Statistical Methods:

Study groups on ordinal and continuous outcomes were compared using the Kruskal-Wallis test with a Steel-Dwass adjustment for pairwise group comparisons for an overall statistical significance criteria of 0.05 for each outcome.

Results

Ear Pinnae:

Thickness of the right ear remained in the range of 0.20-0.25 mm for each of the groups until day 4. Thereafter, the thickness rose sharply for Group treated with imiquimod (Group 1) only, and to a less extent for the other Groups (2-4). The following table shows ear thickness in mm.

| Group | Day 1 | Day 5 | Day 6 | Day 7 |
|---|---|---|---|---|
| 1 (imiquimod only) | 0.21 | 0.28 | 0.37 | 0.40 |
| 2 (20 µg HSP) | 0.23 | 0.28 | 0.33 | 0.34 |
| 3 (100 µg HSP) | 0.22 | 0.25 | 0.28 | 0.29 |
| 4 (carrier cream) | 0.22 | 0.28 | 0.30 | 0.33 |
| 5 (control) | 0.25 | 0.22 | 0.19 | 0.19 |

The results show that HSP used in co-therapy with imiquimod is effective in reducing or even avoiding the occurrence of a side-effect of imiquimod (swelling).

Epidermal Thickness:

A histology study on the back skin samples taken of the euthanized mice, resulted in the following average epidermal thickness of the treated skin (in μm):

| Group | epidermal thickness |
|---|---|
| 1 (imiquimod only) | 58 |
| 2 (20 μg HSP) | 42 |
| 3 (100 μg HSP) | 40 |
| 4 (carrier cream) | 53 |
| 5 (control) | 10 |

The results show that HSP used in co-therapy with imiquimod is effective in reducing or even avoiding the occurrence of a side-effect of imiquimod (swelling).

PASI-Score:

The results for the cumulative PASI Score on day 7 were as follows:

| Group | PASI score |
|---|---|
| 1 (imiquimod only) | 6.5 |
| 2 (20 μg HSP) | 1.7 |
| 3 (100 μg HSP) | 3.0 |
| 4 (carrier cream) | 3.5 |
| 5 (control) | 0 |

The results support that HSP can be used to reduce psoriasis area and severity.

Visual Appearance:

FIG. 1 shows the backs of one mouse of each of groups 1-4 after 6 days of treatment. From left to right: Group 2 (20 μg HSP), Group 3 (100 μg HSP), Group 4 (carrier cream only) and Group 1 (imiquimod only)

As illustrated by FIG. 1, the backs of the mice treated with imiquimod in co-therapy with HSP were still essentially free of scaling, whereas the mice treated with imiquimod only were severely scaled. Increased scaling was also observed in mice treated with carrier cream only, compared to the mice treated in accordance with the invention.

The invention claimed is:

1. A method for therapeutic treatment of psoriasis comprising administering to a patient in need thereof a healthcare product comprising (i) a component selected from the group consisting of heat shock proteins (Hsp) from alfalfa, the product further comprising imiquimod or a pharmaceutically acceptable salt or derivative thereof, wherein the healthcare product comprises an effective amount of at least 0.2 mg/mL of heat shock protein from alfalfa, and 0.1-10 wt % of imiquimod or a pharmaceutically acceptable salt or derivative thereof and wherein the selected heat shock protein alleviates a negative-side effect of imiquimod or a pharmaceutically acceptable salt or derivative thereof.

2. The method of claim 1, wherein the negative side effect is selected from the group consisting of erythema, scaling of the skin, and thickening of the skin.

3. The method of claim 1, wherein the Hsp is included in a first healthcare composition and the imiquimod is included in a second healthcare composition and wherein the first healthcare composition and the second healthcare composition are administered, and wherein at least the second healthcare composition is applied to the skin.

4. The method of claim 1, wherein the Hsp and the imiquimod are administered simultaneously.

5. The method of claim 1, wherein the heat shock protein is Hsp 70.

* * * * *